United States Patent [19]

Verkaart

[11] Patent Number: 5,713,864
[45] Date of Patent: Feb. 3, 1998

[54] INTEGRAL CONDUCTIVE POLYMER RESISTANCE HEATED TUBING

[75] Inventor: Wesley H. Verkaart, Duxbury, Mass.

[73] Assignee: SIMS Level 1, Inc., Rockland, Mass.

[21] Appl. No.: 420,165

[22] Filed: Apr. 11, 1995

[51] Int. Cl.⁶ ............................................. A61F 7/12
[52] U.S. Cl. .................... 604/113; 604/114; 604/43; 604/280; 392/472; 392/478; 165/165; 165/180; 165/185; 165/905; 606/27
[58] Field of Search ........................... 604/264, 265, 604/280, 114, 113, 43; 606/21, 27, 31, 32; 607/2, 63, 33; 165/905, 164, 165, 167, 180, 185, DIG. 4; 137/341; 219/525, 528, 530, 539, 540; 392/472, 478, 480, 482

[56] References Cited

U.S. PATENT DOCUMENTS

| | | |
|---|---|---|
| 1,995,302 | 3/1935 | Goldstein . |
| 2,274,839 | 3/1942 | Marick . |
| 2,883,513 | 4/1959 | Schnabel . |
| 3,355,572 | 11/1967 | Chrow . |
| 3,413,442 | 11/1968 | Buiting et al. . |
| 3,525,967 | 8/1970 | Stauber . |
| 3,582,968 | 6/1971 | Buiting et al. . |
| 4,156,127 | 5/1979 | Sako et al. . |
| 4,180,723 | 12/1979 | Szupillo . |
| 4,455,474 | 6/1984 | Jameson et al. . |
| 4,686,354 | 8/1987 | Makin . |
| 4,725,713 | 2/1988 | Lehrke . |
| 4,798,230 | 1/1989 | Hopperdietzel . |
| 5,022,459 | 6/1991 | Chiles et al. . |
| 5,063,994 | 11/1991 | Verkaart . |
| 5,257,977 | 11/1993 | Eshel ........................... 604/113 |

OTHER PUBLICATIONS

The Merck Index, 10th Edition, 1983 p. 1095.

Primary Examiner—Corrine M. McDermott
Assistant Examiner—Ronald K. Stright, Jr.
Attorney, Agent, or Firm—Dickinson, Wright, Moon, Van Dusen & Freeman

[57] ABSTRACT

A flexible, integral polymer resistance heated conduit is provided that is particularly suitable for use with physiological fluids. The conduit is highly effective in uniformly heating a fluid and in maintaining the fluid at a uniform, predetermined temperature. The conduit is inexpensive and easy to manufacture, and is at least partially transparent or translucent, thereby allowing easy viewing of its contents.

29 Claims, 3 Drawing Sheets

INTEGRAL CONDUCTIVE POLYMER RESISTANCE HEATED TUBING

FIELD OF THE INVENTION

This invention relates to the art of heating physiological fluids for intravenous application to a patient. In particular, the invention is a conduit suitable for physiological uses. The walls of the conduit comprise a section made of an electrically conductive polymer and a portion made of a transparent or translucent polymer. The conductive portion may be heated by electric resistance, and the transparent portion allows the user to view the progress of fluid through the conduit.

BACKGROUND OF THE INVENTION

It is common to heat a physiological solution to normal body temperature before introducing it to the bloodstream intravenously. When the infusion rate is low, however, the heated solution often cools substantially before reaching the patient. One answer to this problem is to provide a patient line that is heated along its entire length by a warming fluid, as shown in U.S. Pat. No. 5,063,994 (Verkaart).

Many types of conduits have been proposed for heating a fluid or maintaining it at a predetermined temperature. Several of these conduits use one or more wires embedded in electrically insulating walls of the conduit to heat the fluid by electric resistance in the wires. For example, U.S. Pat. No. 4,455,474 features a hose suitable for conducting hot melt adhesives wherein the walls of the hose contain multiple plys of electrical resistance heating wires and heat detectors. U.S. Pat. Nos. 2,883,513 and 2,274,839 feature hosing with walls made of metal strips embedded in a nonmetallic material. Similarly, U.S. Pat. No. 4,725,713 shows a heating tape embedded in a hosing wall. The heating tape contains wire coiled about an insulating sheet. U.S. Pat. No. 4,686,354 features a delivery hose for a humidifier with a cable wound spirally around its exterior. The cable has embedded within it an electrical resistance heating wire, which maintains the humidifier at a desired operating temperature. U.S. Pat. No. 4,798,230 features plastic hosing with walls having two portions, one being thicker than the other. A conductive wire is disposed longitudinally coextensive with the hose in the thicker portion. U.S. Pat. Nos. 1,995,302 and 4,038,519 feature a flexible tube suitable for medical uses in which heating is provided by means of wires or strips of a resistance heating conductor embedded in a helical fashion within the walls of the tubing. U.S. Pat. No. 3,355,572 discloses a composite tubing in which heating wires are wound spirally around the inner layer of the tubing and are embedded in the outer layer of the tubing.

While some of the above-mentioned devices are appropriate for their particular uses, they tend to heat in a linear, or local manner, resulting in local overheating of the fluid in the conduit. This effect is inconsequential in many applications. A problem arises, however, when heating a physiological fluid, such as blood, because it begins to degrade at temperatures of about 114° F. Because blood must be heated to body temperature (about 98.5° F.) to achieve optimal results, the conduit must be capable of heating blood uniformly and maintaining its temperature within a narrow range.

Local overheating is reduced when the wiring is closely wound, but this leads to an increase in total resistivity and associated difficulties in controlling the amount of heating. Therefore, conduits containing tightly wound heating elements are unsuitable for use with physiological fluids, due to their inability to accurately maintain a fluid within a given temperature range. Furthermore, as with any embedded wire configuration, the heating density per output power of the wire at the heating wire surface is often so high that the wire becomes excessively heated, resulting in degradation of the surrounding wall material.

Some prior art conduits are designed to be self regulating, so that heating is shut off when a desired temperature is maintained, thus avoiding local over heating of the fluids they carry. Many of these devices have conduit walls constructed of a polymer and a filler with wires embedded in the walls. U.S. Pat. Nos. 3,413,442 and 3,582,968, for example, disclose electrical heating devices whose walls comprise a plastic material having a positive temperature resistivity coefficient, such as carbon black filled, cross-linked polyethylene, and strips or layers of a conductive material such as copper foil or silver. U.S. Pat. No. 5,022,459 describes hosing which may be embedded in concrete or asphalt and used to melt ice or snow on road surfaces. Wires constructed of an electrically conductive material are embedded in the walls of the hosing, and the outer surface of the hosing optionally contains a polymeric material with graphite incorporated into it. While some of these materials are thermally self-regulating, they suffer many of the infirmities associated with other types of embedded wire conduits. These infirmities include degradation of the surrounding wall material caused by the high heating density at the surface of the wire. In addition, the fillers contemplated by these references, e.g., carbon black, render these conduits opaque, which is undesirable in a medical setting where visual verification of fluid flow is important.

Many prior art conduits, such as those in which the conduit walls incorporate powders of metals such as copper, are susceptible to chemical corrosion, especially in acidic or basic environments. Furthermore, metal powders often catalyze undesirable side reactions when they come into contact with physiological solutions. In an effort to avoid this problem, some prior art conduits are made of materials that are chemically inert and highly resistant to corrosion. For example, the conduits disclosed in U.S. Pat. No. 4,180,723 have walls made of conductive carbon filled glasses. While these conduits are very resistant to chemical corrosion and heat degradation, they are inflexible and brittle, and tend to be opaque. These features make them ill-suited to physiological uses where flexibility and transparency or translucency is required.

U.S. Pat. No. 4,156,127 discloses composite tubing which contains at least one layer of carbon loaded PTFE. This type of conduit is flexible and avoids some of the problems associated with thermal degradation. However, it suffers the disadvantage of being opaque. Furthermore, the heating of the conduit as a function of temperature and time indicates that the conduit is prone to local overheating before effective temperature regulation is achieved (see, e.g., FIG. 6). As previously indicated, local overheating is undesirable where physiological fluids are concerned.

It is therefore an object of the present invention to provide a conduit suitable for physiological uses which is flexible and at least partially transparent or translucent, and which is resistant to local overheating, chemical corrosion, and thermal degradation.

SUMMARY OF THE INVENTION

The present invention is a flexible, integral polymer resistance heated conduit that is particularly suitable for use with physiological fluids for uniformly heating the fluids and maintaining them at a predetermined temperature. The preferred embodiment of the invention includes a conduit that is made of at least two types of polymeric materials. The first material is transparent to allow the user to view the contents of the conduit for determining whether fluid is or is not flowing in the conduit. In this application "transparent" means that the presence of the fluid can be viewed through the material and includes "translucent" or similar properties. A second material is conductive and is heated by ohmic resistance When electric current is passed through it. The two materials are in intimate contact and are preferably coextruded to transfer heat from the conductive sections to the other sections. Connection devices, such as luer connectors, may be attached to either end to facilitate easy attachment to known catheters and sources of fluids. Thus, the conduit used with the invention is inexpensive, easy to manufacture, and is suitable for use in the medical environment because it allows one to view its contents.

Because the heat exchanger is in contact with the circulatory system of the patient, the electric current is applied at a frequency that does not adversely affect the heart or other organs. In the preferred embodiment, the electric current is supplied at a frequency of about 400 Hz. Frequencies above 400 Hz permit more leakage current while remaining within published guidelines. Other frequencies may be found to be practical.

DETAILED DESCRIPTION OF THE PREFERRED EMBODIMENTS

Figure 1:
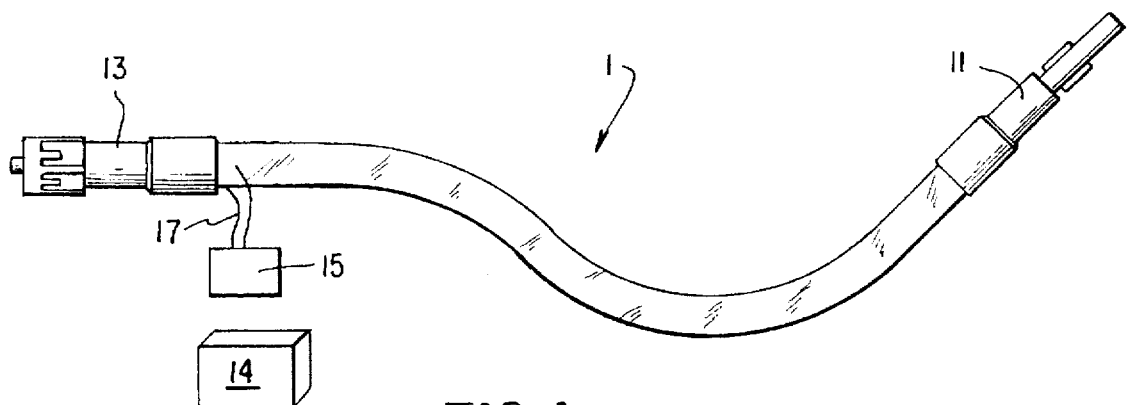
FIG. 1 is a perspective view of a conduit in accordance with the present invention fitted with luer connectors.

FIG. 1 shows a conduit 1 in accordance with the present invention. The conduit is flexible and is especially designed for warming and transporting physiological fluids. As such, the conduit may be provided with luer fittings 11 and 13 to connect to a catheter, an extension line, a bag spike, or the like, for connection to a supply of physiological fluid and to a patient. Luer fittings allow the conduit to be attached quickly and easily to existing hospital equipment.

Also illustrated in FIG. 1 is an electrical connector 15, which is attached to the conduit by electrical leads 17. Connector 15 may be any of several known designs and attaches the conductive parts of the conduit to a source of electric current 14. The leads 17 may be connected to the conductive portion in several ways. For example, wires may be inserted into the polymer after heating (e.g., electrically or ultrasonically). Alternatively, foil strips may be secured to the conductive polymer, for example, by trapping the foil against the conductive polymer with heat shrinkable tubing or overmolding the foil-conductive polymer joint with additional polymer.

Preferably the leads 17 extend from the same end of the conduit, as shown, to simplify the attachment. Of course, leads 17 may be attached to respective opposite ends of the conduit. To locate the leads at the same end of the conduit, the conductive polymer parts should be arranged such that a complete circuit is established by connection at one end. To do this, a separate conductor may be provided to connect a lead to the opposite end of the conductive polymer. Preferably, however, the conductive portions are arranged to provide a complete circuit with connection at one end as will be described with respect to FIG. 2b.

Figure 1A:
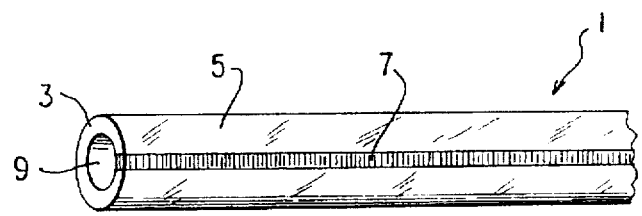
FIGS. 1a, 1b, and 1c are partial perspective views of embodiments of a conduit in accordance with the invention.
Figure 1B:
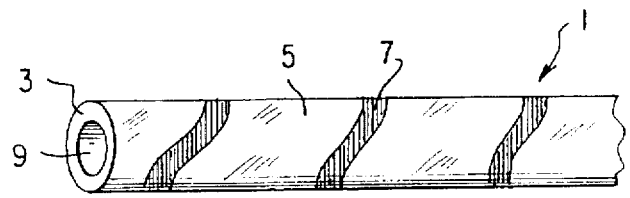
Figure 1C:
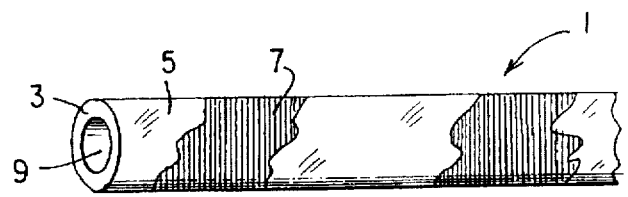

With reference to FIGS. 1a, 1b, and 1c, the conduit of the present invention has a flexible tubular wall 3, which includes a first portion 5 made of a transparent polymeric material and a second portion 7 made of a conductive polymeric material. The tubular walls of the conduit provide an interior space 9 for accommodating the fluid, such as a blood product to be supplied intravenously to a patient.

In the embodiment of FIG. 1a, the conductive polymeric portion 7 is linear and extends along the length of the conduit. In the embodiment of FIG. 1b, however, the conductive polymeric portion is helically disposed along the conduit. FIG. 1c illustrates an embodiment wherein the conductive portion is also helically disposed about the length of the conduit, but wherein the border between the conductive and nonconductive portions is uneven. Other arrangements are possible, the relative placement of the conductive and nonconductive polymeric portions being designed for the particular application.

FIGS. 2 through 7 are transverse cross-sections of various embodiments of a conduit in accordance with the present invention. As noted, the walls of the conduit encompass an interior space 9, through which a fluid to be warmed passes. Preferably, the interior surface 19 and exterior surface 21 of the conduit define an annulus. Other geometries may, however, be suitable or desirable for specific applications. For example, the conduit could be made with a rectangular cross-section.

Figure 2A:
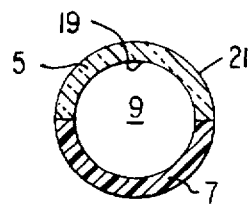
FIGS. 2a and 2b are transverse cross-sections of an embodiment of the invention wherein the walls of the conduit include alternating portions of conductive and transparent polymeric material.
Figure 2B:
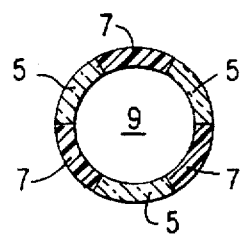

FIGS. 2a and 2b illustrate an embodiment wherein the wall of the conduit is made of alternating segments of conductive and nonconductive polymeric material. The conductive and nonconductive materials may be coextruded through a multimanifold die or by other suitable methods known to the art. See, e.g., J. Kroschwitz, "Concise Encyclopedia Of Science And Engineering", 364–65 (1990), the disclosure of which is incorporated herein by reference. While it is preferred that the boundary between the conducting and insulating segments be sharply defined, the present invention also contemplates embodiments in which the boundary is diffuse. Such a boundary may be advantageous, for example, in embodiments in which a sharply defined boundary would lead to local overheating.

An advantage of the embodiment of FIG. 2b is that the arrangement of conductive segments 7 lends itself to connection of electric current at only one end. Thus, the segments 7 may be bridged at the end opposite leads 17 (e.g., by a "jumper") to provide electric flow down two of the segments and back through the third one of the segments. Of course, such an arrangement would be designed to avoid an excess of current flow in any of the segments, and it may also be desirable to have an even number of segments.

Figure 3A:
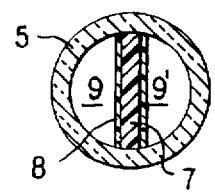
FIGS. 3a and 3b are transverse cross-sections of an embodiment of the invention wherein the walls of the conduit are made of a transparent, nonconductive polymeric material, and wherein the interior of the conduit is divided into two or more portions by segments of conductive polymeric material attached to the interior surfaces of the walls.
Figure 3B:
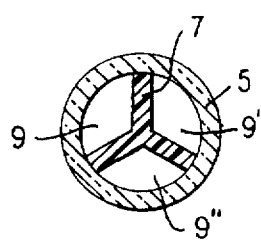

FIGS. 3a and 3b illustrate an embodiment wherein the conductive polymeric portion 7 extends into the interior space of the conduit to divide the interior of the conduit into a plurality of passageways 9, 9', and 9". In this embodiment, the conductive polymeric portion extends completely across the conduit in either a flat or angular configuration. This construction may be useful, for example, in an environment in which it is desirable to keep two fluids in thermal contact, but physically separated from one another. In addition, this embodiment is desirable because it increases the contact area between the conductive portion and the physiological fluid. In appropriate situations, as when the physiological fluid is saline solution or another conductive fluid, the conductive portion may be coated with a thin layer 8 of bio-compatible, electrically insulating material.

Figure 4A:
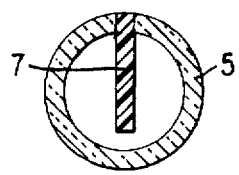
FIGS. 4a through 4c are transverse cross-sections of an embodiment of the invention wherein the walls of a conduit include a transparent nonconductive polymeric material and a conductive polymeric material that protrudes from the exterior surface of the conduit into the interior of the conduit.
Figure 4B:
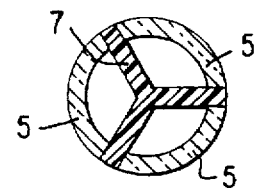
Figure 4C:
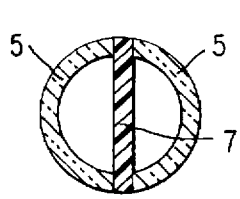

FIGS. 4a through 4c illustrate embodiments of the present invention in which the conductive portion extends from the exterior of the conduit into the interior of the conduit, in configurations similar to those of FIGS. 3a and 3b. This embodiment allows electrical terminals to be attached to the exterior of the conduit at multiple points along its length, while at the same time increasing the surface area of the conductive portion exposed to the fluid within the conduit.

Figure 5A:
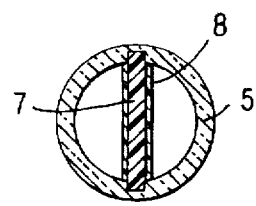
FIGS. 5a, 5b and 5c are transverse cross-sections of an embodiment of the invention wherein the walls of the conduit are made of a transparent or translucent material, and wherein the interior of the conduit is provided with a portion of conductive polymeric material having at least one end embedded in the walls of the conduit.
Figure 5B:
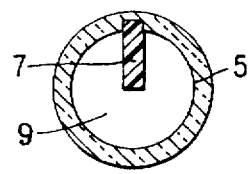
Figure 5C:
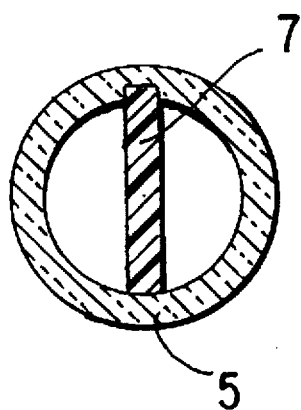

FIGS. 5a, 5b and 5c show embodiments of the invention in which at least part of the conductive portion 7 is only partly embedded in the nonconductive walls 5 of the conduit. This configuration lends greater stability to the conduit in cases where the conducting and insulating portions of the conduit are made out of materials that have a weak affinity for each other, causing the bonding between the two materials at the interface to be relatively weak.

Figure 6:
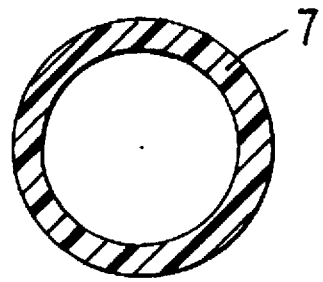
FIG. 6 is a transverse cross-section of an embodiment of the invention wherein the wall of a conduit is made of a conductive polymeric material that is transparent or translucent.

FIG. 6 shows an embodiment wherein the entire wall of the conduit is made of an electrically conductive material that is transparent or translucent. In the event that the wall material is not physiologically suitable, a coating of a physiologically acceptable material may be deposited on the interior surface of the conduit. In addition, if it is desirable to shield the fluid within the conduit from the electrical current, a layer of insulating material may be deposited on the interior surface of the conduit.

Figure 7A:
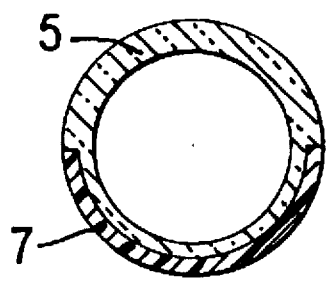
FIGS. 7a and 7b are transverse cross-sections of an embodiment of the invention wherein a conductive polymeric material is embedded in the exterior surface of a transparent polymeric material.
Figure 7B:
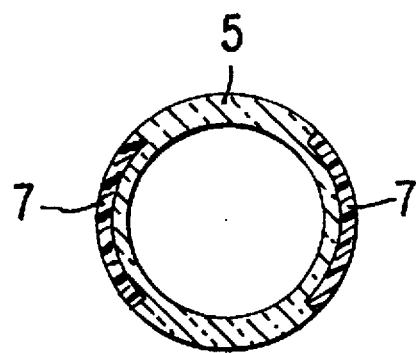

FIGS. 7a and 7b illustrate yet another embodiment of the present invention wherein the conductive portion 7 is embedded in the exterior surface of the transparent portion 5 of the conduit. This embodiment is particularly suitable for providing ready access to the conductive material at several points along the length of the conduit. This embodiment is also useful for providing an insulating barrier between the conductive portion and the solution in the interior of the conduit.

The conductive materials suitable for use in the present invention are flexible polymeric materials that behave as resistance heaters when an electric potential is applied across them. Such materials are well known to the art and include, for example, polyethylene, polyvinylchloride (PVC) or polytetrafluoroethylene (PTFE) loaded with carbon or a metal powder such as silver. U.S. Pat. No. 4,156,127 describes the manufacture of these types of materials. Preferably, the material selected as a conductive polymer is capable of being extruded into various geometries to facilitate the manufacture of the final product.

While most known conductive polymeric materials are opaque, the invention also contemplates the use of conductive polymers that are clear or translucent. The advantage of such materials is that they provide a clear, unobstructed view of the fluid passing through the conduit.

The conduit of the present invention may be equipped with regulating means for controlling the amount of resistance heating provided by a conductive polymer. Many suitable regulating means are known to the art, and include both external means, such as capacitors and rheostats that are used to control the potential applied across the conductive portion, and internal means, as by controlling the degree of cross-linking in the polymer and the amount of carbon or metallic filler used. An example of the latter means is provided in U.S. Pat. No. 3,413,442. The regulating means may be activated by temperature probes which monitor the temperature of the fluid within the conduit at one or more sampling points.

The material selected for the nonconductive portion of the conduit wall is a flexible, polymeric material that is transparent or translucent. Many such materials are known to the art, and include, for example, silicone elastomers, natural or synthetic rubbers, polyolefins, and polyurethanes. The term "polymeric material" includes materials comprising copolymers or mixtures and blends of two or more polymers, and also contemplates the use of pigments or additives as are known to the art. Preferably, the polymer or polymers used in making the nonconductive portion of the conduit are capable of coextrusion with the conductive polymeric material to facilitate the easy manufacture of the final product in any desired shape or design.

The present invention also contemplates the use in any of its embodiments of a lining material deposited on the innermost portion of the conduit walls. The lining material allows the walls of the conduit to be composed of materials that are not suitable for contact with physiological fluids. Thus, for example, if the conductive material is made from a polymer filled with a metal powder, the lining material will prevent undesirable reactions between the metal powder and the physiological fluid.

The conduit of the present invention is designed for general use with physiological fluids, and is specifically designed for use as a patient line that extends substantially the entire distance from the source of fluid to the catheter in contact with a patient. Examples of some physiological fluids with which the invention may be used include blood, lymph fluid, saline solutions, and pharmaceutical mixtures. However, the present invention also has applications outside of the medical field, and is generally useful in any situation where it is desired to uniformly heat a fluid and maintain it at a predetermined temperature. Thus, for example, the conduit of the present invention is useful as a conduit for chemical reactants or solvents in industrial processes where the temperature of the reactants or solvents is crucial and must be carefully controlled. In such applications, the interior of the conduit may be lined with a material that is chemically inert to, and insoluble in, the fluid within the conduit.

Modifications within the scope of the present invention will be obvious to those skilled in the art. Therefore, the scope of the present invention should be determined solely by reference to the appended claims.

I claim:

1. Apparatus for heating fluid passing therethrough comprising an exposed flexible conduit comprising a wall made of a polymeric material for placing in contact with said fluid, a portion of said wall being transparent for allowing a presence of said fluid in said conduit to be viewed from outside said conduit and through said wall, the wall including an electrically conductive polymeric material portion capable of producing resistance heat by the passage of electric current;

a first connector means for supplying fluid to a patient;

a second connector means for receiving said fluid from supply of physiological fluid.

2. The apparatus of claim 1 wherein said flexible conduit comprises said transparent portion as a first portion of said wall and a second portion as said electrically conductive polymeric material portion.

3. The apparatus of claim 2, wherein said conductive portion is a carbon-filled polymer.

4. The apparatus of claim 3, wherein said carbon-filled polymer comprises polyvinylchloride.

5. The apparatus of claim 2, wherein said conductive portion divides an interior of said conduit into a plurality of passageways.

6. The apparatus of claim 5, wherein said conductive portion extends from at least one point on an interior surface of said wall to at least one other distinct point on the interior surface of said wall.

7. The apparatus of claim 5, wherein said conductive portion extends from at least one point on an exterior surface of said wall to at least one other distinct point on the exterior surface of said wall.

8. The apparatus of claim 5, wherein said conductive portion extends from a plurality of distinct points on an interior surface of said wall to at least one point on the interior surface of said wall.

9. The apparatus of claim 5, wherein said conductive portion extends from a plurality of distinct points on an exterior surface of said wall to at least one distinct point on the exterior surface of said wall.

10. The apparatus of claim 5, wherein said conductive portion extends from at least one point within said wall to at least one other distinct point within said wall.

11. The apparatus of claim 5, wherein said conductive portion extends from at least one point within said wall to at least one other point on an interior surface of said wall.

12. The apparatus of claim 5, wherein said conductive portion extends from at least one point on an exterior of said wall to at least one other point within an interior of said conduit.

13. The apparatus of claim 5, wherein said conductive portion extends from at least one point within said wall to within an interior of said conduit.

14. The apparatus of claim 5, wherein said passageways run the length of said conduit and each passageway is separate from other passageways.

15. The apparatus of claim 2, wherein at least part of said conductive portion protrudes from an outer surface of said wall into an interior of said conduit.

16. The apparatus of claim 1, wherein said wall further comprises a physiologically compatible material deposited on an interior surface of said wall.

17. Apparatus for heating a physiological fluid supplied to a patient comprising:

a flexible conduit for carrying said fluid and being in thermal contact with said fluid, at least a portion of a wall section of said conduit being transparent for allowing a presence of said fluid in said conduit to be viewed from outside said conduit and through said wall section, a portion of said conduit being made of an electrically conductive polymeric material capable of producing resistance heat by the passage of electric current, first means for connecting one end of said conduit to means for allowing said fluid to be infused into said patient, second means for connecting an opposite end of said conduit to a source of said fluid, and means for connecting said polymeric material to a source of said electric current.

18. Apparatus according to claim 17 wherein said flexible conduit comprises a first portion and a second portion, wherein said first portion comprises said transparent portion of said wall section and said second portion is said portion made of said electrically conductive polymeric material capable of producing resistance heat by the passage of electric current.

19. Apparatus according to claim 18 wherein said flexible conduit comprises a flexible wall forming an interior space and said second portion extends into said interior space.

20. Apparatus according to claim 19 wherein said second portion extends completely across said interior space to divide said space into a plurality of passageways.

21. Apparatus according to claim 19 wherein at least an end of said second portion is embedded in said first portion.

22. Apparatus according to claim 18 wherein said flexible conduit comprises a flexible wall comprising circumferentially alternating segments of said first and second portions.

23. Apparatus according to claim 18 wherein said flexible conduit comprises a flexible wall comprising said second portion embedded in said first portion.

24. Apparatus according to claim 17 further comprising said source of electric current, wherein said source of electric current is capable of providing said electric current at a frequency that does not adversely affect the heart or other organs of the patient.

25. Apparatus according to claim 24 wherein said source of electric current is capable of providing said electric current at a frequency of about 400 Hz.

26. Apparatus according to claim 17 further comprising a physiological compatible coating covering at least a portion of an interior of said conduit.

27. A flexible conduit for carrying and heating a physiological fluid in a passageway to a patient comprising:

a) a flexible conduit having a conduit wall comprising an exposed conduit outer surface and a passageway inner surface, said conduit wall forming said passageway for carrying said fluid;

b) at least a portion of said conduit wall being transparent for allowing a presence of said fluid in said passageway to be viewed from outside said conduit and through said portion of the conduit wall; and c) at least a portion of said conduit being made of an electrically conductive polymeric material capable of producing resistance heat by the passage of electric current therethrough, passage of electric current through said polymeric material heating said fluid.

28. Apparatus for heating fluid passing therethrough comprising an exposed flexible conduit comprising a wall made of a polymeric material fox placing in contact with said fluid, a portion of said wall being transparent for allowing a presence of said fluid in said conduit to be viewed from outside said conduit and through said wall, the wall including an electrically conductive polymeric material portion capable of producing resistance heat by the passage of electric current.

29. Apparatus for heating fluid passing therethrough comprising an exposed flexible conduit comprising a wall made of a polymeric material for placing in contact with said fluid, a portion of said wall being transparent for allowing a presence of said fluid in said conduit to be viewed from outside said conduit and through said wall, the wall including an electrically conductive polymeric material portion capable of producing resistance heat by the passage of electric current, wherein said flexible conduit comprises said transparent portion as a first portion of said wall and a second portion as said electrically conductive polymeric material portion, said second portion dividing an interior of said flexible conduit into a plurality of passages.

* * * * *